United States Patent [19]
Cooke et al.

[11] Patent Number: 5,428,070
[45] Date of Patent: Jun. 27, 1995

[54] TREATMENT OF VASCULAR DEGENERATIVE DISEASES BY MODULATION OF ENDOGENOUS NITRIC OXIDE PRODUCTION OF ACTIVITY

[75] Inventors: John P. Cooke, Palo Alto; Victor J. Dzau, Los Altos Hills; Gary H. Gibbons, Palo Alto, all of Calif.

[73] Assignee: The Board of Trustees of the Leland Stanford Jr. Univ., Stanford, Calif.

[21] Appl. No.: 76,312

[22] Filed: Jun. 11, 1993

[51] Int. Cl.⁶ ..................... A01N 37/00; A61K 31/19
[52] U.S. Cl. ................................. 514/557; 514/310
[58] Field of Search ............................. 514/310, 557

[56] References Cited

PUBLICATIONS

Andrews et al., "Low-density Lipoproteins inhibit endothelium-dependent Relaxation in Rabbit Aorta", *Nature*, 327:237–239 (1987).

Bath et al., "Nitric Oxide and Prostacyclin: Divergence of Inhibitory Effects on Monocyte Chemotaxis and Adhesion to Endothelium in Vitro", *Arteriosclerosis and Thrombosis*, 11(2):254–260 (1991).

Cooke, "Endothelial Dysfunction in Disease States", *Current Opinion in Cardiology*, 5:637–644 (1990).

Drexler et al., "Correction of Endothelial Dyfunction in Coronary Microcirculation of Hypercholesterolaemic Patients", *The Lancet*, 338:1546–1550 (1991).

Garg and Hassid, "Nitric Oxide-generating Vasodilators and 8-Bromo-Cyclic Guanosine Monophosphate Inhibit Mitogenesis and Proliferation of Cultured Rat Vascular Smooth Muscle Cells", *J. Clin. Invest.*, 83:1774–1777 (1989).

Girerd et al., "L-Arginine Augments Endothelium-Dependent Vascodilation in Cholesterol-Fed Rabbits", *Circulation Research*, 67(6):1301–1308 (1990).

Heistad et al., "Augmented Responses to Vasoconstrictor Stimuli in Hypercholesterolemic and Atherosclerotic Monkeys", *Circulation Research*, 54(6)711–718 (1984).

Kubes et al., "Nitric Oxide: An Endogenous Modulator of Leukocyte Adhesion", *Proc. Natl. Acad. Sci. USA*, 88:4651–4655 (1991).

Kugiyama et al., "Impairment of Endothelium-dependent Arterial Relaxation by Lysolectithin in Modified Low-density Lipoproteins", *Nature*, 344:160–162 (1990).

Kuo et al., "Pathophysiological Consequences of Atherosclerosis Extend Into the Coronary Microcirculation: Restoration of Endothelium-dependent Responses by L-Arginine", *Circulation Research*, 70(3):465–476 (1992).

Lefer et al., "Role of Endothelium-derived Relaxing Factor as a Cardioprotective Agent in Myocardial Ishemia", *Basil, Karger*, pp. 190–197 (1990).

Minor et al., "Diet-induced Atherosclerosis Increases the Release of Nitrogen Oxides from Rabbit Aorta", *J. Clin. Invest.*, 86:2109–2116 (1990).

(List continued on next page.)

*Primary Examiner*—Werren B. Lone
*Attorney, Agent, or Firm*—Bertram I. Rowland

[57] ABSTRACT

Atherogenesis and restenosis are treated by long term administration of physiologically acceptable compounds which enhance the level of endogenous nitric oxide in the host. Alternatively, or in combination, other compounds may be administered which provide for short term enhancement of nitric oxide, either directly or by physiological processes. In addition, cells may be genetically engineered to provide a component in the synthetic pathway to nitric oxide, so as drive the process to enhance nitric oxide concentration, particularly in conjunction with the administration of a nitric oxide precursor.

5 Claims, No Drawings

PUBLICATIONS

Mitchell et al., "Native LDL Inhibits the Release of Endothelial Derived Relaxing Factor by Reducing the Activity of Endothelial Nitric Oxide Synthase", (Abstract), *J. Vasc. Res.*, 29:169 (1992).

Pohl and Busse, "EDRF Increases Cyclic GMP in Platelets During Passage Through the Coronary Vascular Bed", *Circulation Research*, 65(6):1798–1803 (1989).

Radomski et al., "Comparative Pharmacology of Endothelium-derived Relaxing Factor, Nitric Oxide and Prostacyclin in Platelets", *Br. J. Pharmacol.*, 92:181–187 (1987).

Ross, "The Pathogenesis of Atherosclerosis—an Update", *The New England Journal of Medicine*, 314(8):488–500 (1986).

Rossitch, Jr. et al., "L-Arginine Normalizes Endothelial Function in Cerebral Vessels from Hypercholesterolemic Rabbits", *J. Clin. Invest.*, 87:1295–1299 (1991).

Stamler et al., "N-Acetylcysteine Potentiates Platelet Inhibition by Endothelium-derived Relaxing Factor", *Circulation Research*, 65(3):789–795 (1989).

Tanner et al., "Oxidized Low Density Lipoproteins Inhibit Relaxations of Porcine Coronary Arteries: Role of Scavenger Receptor and Endothelium-derived Nitric Oxide", *Circulation*, 83(6):2109–2116 (1991).

Tomita et al., "Rapid and Reversible Inhibition by Low Density Lipoprotein of the Endothelium-dependent Relaxation to Hemostatic Substances in Porcine Coronary Arteries", *Circulation Research*, 66(1):18–27 (1990).

Weidinger et al., "Persistent Dysfunction of Regenerated Endothelium After Balloon Angioplasty of Rabbit Iliac Artery", *Circulation*, 81(5):1667–1679 (1990).

Yamamoto et al., "Videomicroscopic Demonstration of Defective Cholinergic Arteriolar Vasodilation in Atherosclerotic Rabbit", *J. Clin. Invest.*, 81:1752–1758 (1988).

TREATMENT OF VASCULAR DEGENERATIVE DISEASES BY MODULATION OF ENDOGENOUS NITRIC OXIDE PRODUCTION OF ACTIVITY

INTRODUCTION

This invention was supported in part by the United States Government under Grant 1KO7HCO266((NH-LBI). The U.S. Government may have an interest in this application.

TECHNICAL FIELD

The field of this invention is the treatment of vascular degenerative diseases, particularly atherosclerosis and restenosis.

BACKGROUND

Atherosclerosis and vascular thrombosis are a major cause of morbidity and mortality, leading to coronary artery disease, myocardial infarction, and stroke. Atherosclerosis begins with an alteration in the endothelium, which lines the blood vessels. The endothelial alteration results in adherence of monocytes, which penetrate the endothelial lining and take up residence in the subintimal space between the endothelium and the vascular smooth muscle of the blood vessels. The monocytes absorb increasing amounts of cholesterol (largely in the form of oxidized or modified low-density lipoprotein) to form foam cells. Oxidized low-density lipoprotein (LDL) cholesterol alters the endothelium, and the underlying foam cells distort and eventually may even rupture through the endothelium.

Platelets adhere to the area of endothelial disruption and release a number of growth factors, including platelet derived growth factor (PDGF). PDGF, which is also released by foam cells and altered endothelial cells, stimulates migration and proliferation of vascular smooth muscle cells into the lesion. These smooth muscle cells release extracellular matrix (collagen and elastin) and the lesion continues to expand. Macrophages in the lesion elaborate proteases, and the resulting cell damage creates a necrotic core filled with cellular debris and lipid. The lesion is then referred to as a "complex lesion." Rupture of this lesion can lead to thrombosis and occlusion of the blood vessel. In the case of a coronary artery, rupture of a complex lesion may precipitate a myocardial infarction, whereas in the case of a carotid artery, stroke may ensue.

One of the treatments that cardiologists and other interventionalists employ to reopen a blood vessel which is narrowed by plaque is balloon angioplasty (approximately 300,000 coronary and 100,000 peripheral angioplasties are performed annually). Although balloon angioplasty is successful in a high percentage of the cases in opening the vessel, it unfortunately denudes the endothelium and injures the vessel in the process. This damage causes the migration and proliferation of vascular smooth muscle cells of the blood vessel into the area of injury to form a lesion, known as myointimal hyperplasia or restenosis. This new lesion leads to a recurrence of symptoms within three to six months after the angioplasty in a significant proportion of patients (30-40%).

Because of their great prevalence and serious consequences, it is critically important to find therapies which can diminish the incidence of atherosclerosis, vascular thrombosis and restenosis. Ideally, such therapies would inhibit the pathological processes associated with atherosclerosis, thereby providing prophylaxis or retarding the progression of the degenerative process.

As briefly summarized above, these pathological processes are extremely complex, involving a variety of different cells which undergo changes in their character, composition, and activity, as well as in the nature of the factors which they secrete and the receptors that are up- or down-regulated. A substance released by the endothelium, "endothelium derived relaxing factor" (EDRF), may play an important role in inhibiting these pathologic processes EDRF is now known to be nitric oxide (NO) or a labile nitroso compound which liberates NO. (For purposes of the subject invention, unless otherwise indicated, nitric oxide (NO) shall intend nitric oxide or the labile precursor.) This substance has been reported to relax vascular smooth muscle, inhibit platelet aggregations, inhibit mitogenesis and proliferation of cultured vascular smooth muscle, and leukocyte adherence. NO may have other effects, either direct or indirect, on the various cells associated with vascular walls and degenerative diseases of the vessel.

Relevant Literature

Girerd, et al. (1990) Circulation Research 67, 1301–1308 report that intravenous administration of L-arginine potentiates endothelium-dependent relaxation in the hind limb of cholesterol-fed rabbits. The authors conclude that synthesis of EDRF can be increased by L-arginine in hypercholesterolemia. Rossitch, et al. (1991) J. Clin. Invst. 87, 1295–1299 report that in vitro administration of L-arginine to basilar arteries of hypercholesterolemic rabbits reverses the impairment of endothelium-dependent vasodilation and reduces vasoconstriction. They conclude that the abnormal vascular responses in hypercholesterolemic animals is due to a reversible reduction in intracellular arginine availability for metabolism to nitric oxide.

Creager, et al. (1992) J. Clin. Invest. 90, 1248–1253, report that intravenous administration of L-arginine improves endothelium-derived NO-dependent vasodilation in hypercholesterolemic patients.

Cooke, et al., "Endothelial Dysfunction in Hypercholesterolemia is Corrected by L-arginine," Endothelial Mechanisms of Vasomotor Control, eds. Drexler, Zeiher, Bassenge, and Just; Steinkopff Verlag Darmstadt, 1991, pp. 173–181, review the results of the earlier references and suggest, "If the result of these investigations may be extrapolated, exogenous administration of L-arginine (i.e., in the form of dietary supplements) might represent a therapeutic adjunct in the treatment and/or prevention of atherosclerosis."

Cooke, (1990) Current Opinion in Cardiology 5, 637–644 discusses the role of the endothelium in the atherosclerosis and restenosis, and the effect that these disorders have on endothelial function.

Cooke (1992) J. Clin. Invest. 90, 1168–1172, describe the effect of chronic administration of oral L-arginine in hypercholesterolemic animals on atherosclerosis. This is the first demonstration that oral L-arginine supplements can improve the release of NO from the vessel wall. The increase in NO release from the vessel wall was associated with a striking reduction in atherosclerosis in hypercholesterolemic animals. This is the first evidence to support the hypothesis that increasing NO production by the vessel wall inhibits the development of atherosclerosis.

Cooke and Tsao, (1992) Current Opinion in Cardiology 7, 799–804 describe the mechanism of the progression of atherosclerosis and suggest that inhibition of nitric oxide may disturb vascular homeostasis and contribute to atherogenesis.

Cooke and Santosa, (1993) In: Steroid Hormones and Dysfunctional Bleeding, AAAS Press, review the activities of EDRF in a variety of roles and suggest that reversibility of endothelial dysfunction may be affected by the stage of atherosclerosis. They conclude that EDRF is a potent vasodilator, plays a key role in modulating conduit and resistance vessel tone, has important effects on cell growth and interactions of circulatory blood cells with a vessel wall, and that disturbances of EDRF activity may initiate or contribute to septic shock, hypertension, vasospasm, toxemia and atherosclerosis.

Other references which refer to activities attributed to NO or its precursor include: Pohl and Busse (1989) Circ. Res. 65:1798–1803; Radomski et al. (1987) Br. J. Pharmacol. 92:181–1187; and Stamler et al. (1989) Circ. Res. 65:789–795; anti-platelet activity); Garg and Hassid (1989) J. Clin. Invest. 83:1774–1777; and Weidinger et al, (1990) Circulation 81:1667–1679; NO activity in relation to vascular smooth muscle growth); Ross (1986) N. Engl. J. Med. 314:488–500; Bath et al. (1991) Arterioscler. Thromb. 11:254–260; Kubes et al. (1991) Proc. Natl. Acad. Sci. USA 89:6348–6352; Lefer et al. (1990) In: Endothelium-Derived Contracting Factors. Basel, S. Karger, pp. 190–197; NO activity in relation to leukocyte adhesion and migration); Heistad et al. (1984) Circ. Res. 43:711–718; Rossitch et al. (1991) J. Clin. Invest. 87:1295–1299; Yamamoto et al. (1988)ibid 81:1752–1758; Andrews et al. (1987) Nature 327:237–239; Tomita et al. (1990)Circ. Res. 66:18–27; Kugiyama et al. (1990) Nature 344:160–162; Mitchell et al. (1992) J. Vasc. Res. 29:169 (abst.); and Minor et al. (1990) J. Clin. Invest. 86:2109–2116; NO activity in relation to hypercholesterolemia); Tanner et al. (1991) Circulation 83:2012–2020; Kuo et al. (1992) Circ. Res. 70:f465–476; Drexler et al. (1991) Lancet 338:1546–1550; and Nakanishi et al. (1992) In: Scientific Conference on Functional and Structural Mechanisms of Vascular Control, Snowbird, UT, p. 86 (abstsr.); relation of L-arginine to NO-dependent vasodilation.

SUMMARY OF THE INVENTION

Atherosclerosis and restenosis are treated with agents that enhance nitric oxide formation. The enhancement of endogenous nitric oxide formation inhibits the progression of restenosis and atherosclerosis. As a prophylaxis or treatment for atherosclerotic susceptible hosts, the agent is chronically administered at an effective dosage. For restenosis, the agent may be administered for a limited period since this pathological process generally abates 3–6 months after the vascular injury (i.e. angioplasty or atherectomy). Oral administration of L-arginine as a dietary supplement will increase NO elaboration and thereby diminish the effects of atherogenesis. Other techniques to enhance NO production may be utilized such as increasing the availability of NO synthase, for example, as a result of enhanced expression of NO synthase in the vessel wall, particularly at the lesion site.

DESCRIPTION OF SPECIFIC EMBODIMENTS

In accordance with the subject invention, common vascular degenerative diseases such as atherosclerosis, vascular thrombosis, and restenosis, are treated prophylactically and/or therapeutically by maintaining an enhanced level of nitric oxide or its precursor in the vessel wall in accordance with a predetermined regimen over an extended period of time. The enhanced level of nitric oxide (which is intended to include any precursor of nitric oxide which results in such enhanced level) can be achieved by modulating the activity, synthesis or concentration of any of the components associated with the formation of nitric oxide in the nitric oxide synthetic pathway. The enhanced level of nitric oxide may be a result of administration to the patient of an intermediate in the metabolic pathway to the production of nitric oxide (or its physiological equivalent), the enhanced levels of an enzyme associated with the production of nitric oxide, or a physiologically acceptable precursor, which may lead directly or indirectly, to formation of nitric oxide.

One approach is to employ L-arginine as a dietary supplement. This amino acid may be administered as any physiologically acceptable salt, such as the hydrochloride salt, glutamate salt, etc. It may also be administered as a peptide (i.e. poly-L-arginine) so as to increase plasma levels of the NO precursor. Naturally occurring sources include protamine. The administration of L-arginine or other convenient NO precursor would be in accordance with a predetermined regimen, which would be at least once weekly and over an extended period of time, generally at least one month, more usually at least three months, as a chronic treatment, and could last for one year or more, including the life of the host. The dosage administered will depend upon the frequency of the administration, the blood level desired, other concurrent therapeutic treatments, the severity of the condition, whether the treatment is for prophylaxis or therapy, the age of the patient, the natural level of NO in the patient, and the like. Desirably, the amount of L-arginine or biologically equivalent compound which is used would generally provide a plasma level in the range of about 0.2 mM to 30 mM. The oral administration of L-arginine can be achieved by providing L-arginine as a pill, powder, capsule, liquid solution or dispersion, particularly aqueous, or the like. Various carriers and excipients may find use in formulating the NO precursor, such as lactose, terra alba, sucrose, gelatin, aqueous media, physiologically acceptable oils, e.g. peanut oil, and the like. Usually, if daily, the administration of L-arginine for a human host will be about 1 to 12 g per day.

The administration of L-arginine may be administered prophylactically, so as to inhibit atherogenesis or restenosis, or therapeutically after atherogenesis has been initiated. Thus, for example, a patient who is to undergo balloon angioplasty may have a regimen of L-arginine administered substantially prior to the balloon angioplasty, preferably at least about a week or substantially longer. Alternatively, in a patient where atherogenesis is suspected, the administration of L-arginine may begin at any time. Of particular interest is the incorporation of L-arginine as a supplement in a food, such as a health bar, e.g. granola, other grains, fruit bars, such as a date bar, fig bar, apricot bar, or the like. The amount of L-arginine or the equivalent would be about 2–25 g per dosage or bar, preferably about 3–15 g.

Instead of oral administration, intravascular administration may also be employed, particularly where more rapid enhancement of the nitric oxide level in the vascular system is desired (i.e. as with acute thrombosis of a critical vessel), so that combinations of oral and parenteral administrations may be employed in accordance with the needs of the patient. Furthermore, parenteral administration may allow for the administration of compounds which would not readily be transported across the mucosa from the gastrointestinal tract into the vascular system.

For intravascular administration, a wide variety of individual or combinations of physiologically acceptable compositions may be employed, which may be provided systemically or in proximity to a lesion site. Thus, one may provide for combinations of peroxy compounds or other oxygen containing oxidants, where the oxidant is physiologically acceptable, in conjunction with a nitrogen source, such as substituted guanidines, e.g. L-arginine, amidines, or the like. Alternatively, one may reduce the degradation of endogenous nitric oxide using antioxidants (such as sulfhydryl containing compounds) or compounds that prevent the production of oxygen-derived free radicals (such as superoxide dismutase), as it is known that oxygen-derived free radicals (such as superoxide anion) can inactivate nitric oxide. Thiol compounds may also find application, as well as their derivatives, such as disulfides, sulfonic acids, thiol esters, thiono thiol esters, and the like.

Other compounds which may find use include partially oxidized nitrogen compounds, such as hydroxylamines, oxazoles, oxazines, nitroso compounds, or the like. Physiologically acceptable stable free radical compounds, such as nitroxyl compounds, may find use, where the unpaired electron may be on nitrogen or oxygen, analogous to NO. These compounds will be, for the most part, synthetic organic compounds generally having a molecular weight of at least about 100 and usually not more than about 2000 D.

Other compositions which may find use include nitrites, including nitrite esters, e.g. esters of carbonate, thiocarbonate, etc. These compositions may be administered at the site of a lesion to provide for rapid enhancement of nitric oxide concentration, so as to initiate or inhibit the various physiological processes affected by the level of nitric oxide present and associated with plaque formation or restenosis. Particularly, processes associated with the vascular smooth muscle ("VSM") cell proliferation and invasion of the endothelial layer can be modulated.

Alternatively, one can enhance, either in conjunction with the enhancement of precursors to nitric oxides or independently, components of the nitric oxide metabolic pathway. For example, one may enhance the amount of nitric oxide synthetase present in the vessel wall, particularly at the site of lesions. This can be done by local administration to the lesion site or systemically into the vascular system. The synthase may be administered using liposomes, slow release particles, or in the form of a depot, e.g. in collagen, hyaluronic acid, biocompatible gels, vascular stents, or other means, which will provide the desired concentration of the NO-synthase at the lesion site.

Alternatively, cells may be genetically engineered to provide for constitutive or inducible expression of the synthase. Thus, expression vectors (viral or plasmid) may be prepared which contain the NO synthase gene and which can be introduced into host cells which will then produce high concentrations of nitric oxide. These cells may be introduced at the lesion site or at another site in the host, where the increased NO synthase activity will maintain an elevated level of NO in the vascular system.

Cultured cells can be transfected with expression vectors containing the NO synthase gene ex-vivo and then introduced into the vessel wall, using various intra-arterial or intra-venous catheter delivery systems. Alternatively, techniques of in vivo gene transfer can be employed to transfect vascular cells within the intact vessel in vivo. The NO synthase gene can be expressed at high constitutive levels or it can be linked to an inducible promoter (which may have tissue specificity) to allow for regulation of NO synthase expression.

DNA constructs are prepared, where a NO synthase gene is joined to an appropriate promoter, either with its native termination region or a different termination region, which may provide for enhanced stability of the messenger RNA. Constitutive promoters of particular interest will come from viruses, such as Simian virus, papilloma virus, adenovirus, HIV, Rous sarcoma virus, cytomegalovirus or the like, where the promoters include promoters for early or late genes, or long terminal repeats. Endogenous promoters may include the $\beta$-actin promoter, or cell-type specific promoters.

A construct is prepared in accordance with conventional techniques, the various DNA fragments being introduced into an appropriate plasmid or viral vector, normally a vector capable of replication in a bacterial and/or eucaryotic host. Alternatively, the vector will normally include a marker, which allows for selection of cells carrying the vector, e.g. antibiotic resistance. The vector will normally also include an origin which is functional in the host for replication. Other functional elements may also be present in the vector.

Once the vector has been prepared and replicated, it may then be used for introduction into host cells. The plasmid vector construct may be further modified by being joined to viral elements which allow for ease of transfection, may provide a marker for selection, e.g. antibiotic resistance, or other functional elements. Introduction of the plasmid vector construct into the host cells may be achieved by calcium phosphate precipitated DNA, transfection, electroporation, fusion, lipofection, viral capsid-mediated transfer, or the like. Alternatively, the NO synthase construct within viral vectors may be introduced by standard infection techniques. For somatic cell gene therapy, autologous cells will generally be employed, although in some instances allogeneic cells or recombinantly modified cells may be employed. Usually the cells employed for genetic modification will be mature endothelial or vascular smooth muscle cells. Occasionally, the cells employed for genetic modification will be progenitor cells, particularly early progenitor cells. For example, myoblasts may be employed for muscle cells or hematopoietic stem cells or high proliferative potential cells may be employed for lymphoid and/or myelomonocytic cells.

Depending upon the nature of the cells, they may be injected into tissue of the same or different cellular nature, they may be injected into the vascular system, where they may remain as mobile cells or home to a particular site (i.e. the lesion). The number of cells which are administered will depend upon the nature of the cells, the level of production of the synthase, the desired level of NO synthase in the host vascular system, at the lesion site, or the like, whether the enhanced level of synthase is the only treatment or is used in conjunction with other components of the nitric oxide synthetic pathway, and the like. Therefore, the particular number of cells to be employed will be determined empirically in accordance with the requirements of the particular patient.

These cells may also be introduced into the circulation by first growing them on the surface of standard vascular graft material (i.e. Dacron or polytetrafluoroethylene grafts) or other synthetic vascular conduits or vascular bioprostheses.

Alternatively, one may use viral vectors, which are capable of infecting cells in vivo, such as adenovirus or retroviruses. In this case, the viral vector containing the NO synthase gene will be administered directly to the site of interest, where it will enter into a number of cells and become integrated into the cell genome. Thus, one can titer the desired level of nitric oxide synthase which is secreted, by providing for one or more administrations of the virus, thus incrementally increasing the amount of synthase which is secreted. Alternatively, one may use modified liposomes as a vehicle for endovascular administration of the vector containing the NO synthase gene. One such modified liposome technique involves mixing the liposomes with the vector containing NO synthase. Once the NO synthase-containing vector is incorporated into the liposome, the liposomes are coated with a protein (e.g. the viral coat protein of the Hemagglutinating Virus of Japan) that increases the affinity of the liposome for the vessel wall.

In some situations, the NO synthase gene may be co-transfected with an artificial gene encoding an arginine rich polypeptide susceptible to proteolytic cleavage as an intracellular source of L-arginine. In other situations, the NO synthase gene may be co-transfected with the superoxide dismutase gene, so as to inhibit the degradation of the nitric oxide.

In some situations, acute treatment may be involved, requiring one or a few administrations. This will normally be associated with compounds which can act as nitric oxide precursors and are other than naturally occurring compounds or are compounds which may be added with naturally occurring compounds to enhance the rate of formation of nitric oxide. Thus, one may provide for acute administration of L-arginine and superoxide dismutase to increase the nitric oxide concentration over a restricted period of time. These administrations may be independent of or in conjunction with long term regimens.

The following examples are offered by way of illustration and not by way of limitation.

EXPERIMENTAL

EXAMPLE 1

Anti-atherogenic effects of oral arginine:

Study design: (See, Cooke et al., 1992, supra) Male New Zealand white rabbits (n=49) were assigned to one of three treatment groups: 10 were fed with normal rabbit chow for ten weeks (Control); 19 received chow enriched with 1% cholesterol (Chol); and 20 received a 1% cholesterol diet supplemented with 2.5% L-arginine hydrochloride in the drinking water (Arg.). Following ten weeks of the dietary intervention, animals were lightly sedated and the central ear artery cannulated for measurement of intra-arterial blood pressure, followed by collection of blood samples for serum chemistries and plasma arginine. Subsequently the animals were sacrificed and the left main coronary artery and the thoracic aorta were harvested for studies of vascular reactivity and histomorphometry. In some animals, blood was collected for studies of platelet and monocyte reactivity.

Results: Biochemical and physiological measurements. Hypercholesterolemic animals maintained on oral L-arginine supplementation (Arg) experienced a twofold elevation in plasma arginine levels in comparison to animals on a normal (Control) or 1% cholesterol (Chol) diet alone; the elevation in plasma arginine was maintained throughout the course of the study. Serum cholesterol measurements were elevated equally in both groups receiving the 1% cholesterol diet [$50\pm6$ vs. $1629\pm422$ vs. $1852\pm356$ mg/dl respectively for Control (=10), Chol (=13), and Arg (=14)]. There were no significant differences in hemodynamic measurements between groups.

Organ chamber studies of isolated vessels: For NO-independent responses, there were no differences between the treatment groups in maximal response or sensitivity to norepinephrine (a vasoconstrictor), or to nitroglycerin (a nitrovasodilator). By contrast, NO-dependent relaxations were attenuated in vessels harvested from hypercholesterolemic animals with a reduction in the maximal response to acetylcholine, and a reduction in sensitivity to calcium ionophore. In comparison, vessels harvested from hypercholesterolemic animals receiving L-arginine supplementation had improved NO-dependent relaxation. Similarly, sensitivity of vessels to calcium ionophore A23187 was greater in the Arg group. In a separate study, the effect of chronic arginine supplementation to improve NO-dependent relaxation was confirmed in the hypercholesterolemic rabbit abdominal aorta.

Histomorphometric studies (planimetry of EVG-stained sections): A blinded histomorphometric analysis revealed that medial cross-sectional areas of thoracic aortae were not different between the groups. By contrast, the intimal cross-sectional area (i.e. amount of atherosclerotic plaque) of vessels from hypercholesterolemic animals receiving L-arginine supplementation was reduced in comparison to those from animals receiving cholesterol diet alone. In the Arg animals the reduction in the intimal lesion was most pronounced in the ascending thoracic aorta and left main coronary artery. In the left main coronary artery of hypercholesterolemic animals receiving arginine, essentially no atherosclerotic plaque developed.

Changes in lesion surface area: In a second series of studies, the extent of the thoracic aorta involved by lesions was examined. In hypercholesterolemic rabbits receiving vehicle (n=6) or L-arginine supplement (n=6), thoracic aortae (from left subclavian artery to diaphragm) were harvested after ten weeks of treatment, bisected longitudinally, and stained with oil-red O. Vessels were photographed and vessel and lesion surface area determined by planimetry. Approximately 40% of the total surface area was covered with plaque in thoracic aortae from hypercholesterolemic animals receiving vehicle, whereas in thoracic aortae from arginine-treated hypercholesterolemic animals, less than 10% of the surface area was covered with plaque.

To summarize, dietary arginine supplementation increases plasma arginine levels, but does not alter serum cholesterol. This is associated with significant improvement in NO-dependent vasodilation as judged by bioassay. Finally, the improvement in NO-dependent vasodilation is associated with reduction in thickness and area of the lesions in vessels from hypercholesterolemic animals.

EXAMPLE 2

Inhibition of platelet aggregation by oral L-arginine:

The effect of L-arginine supplementation on platelet reactivity in rabbits that had normal chow (Control; n=6), a 1% cholesterol diet (Chol; n=5), or a 1% cholesterol diet supplemented with oral arginine (Arg; n=6), as detailed above, was examined. Arterial blood obtained after central ear artery cannulation was anticoagulated with 13 mM sodium citrate. Platelet-rich suspension was prepared by washing platelets in calcium-free Krebs-Henseleit solution and resuspending them in Tyrode's solution with albumin. The platelet count was adjusted at $2.5 \times 10^4$ platelets/$\mu$l by addition of platelet-poor plasma. Aggregation was initiated by addition of adenosine diphosphate and monitored by standard nephelometric techniques. In platelets derived from Chol animals, aggregation was not different in rate or maximum extent in comparison to platelets from Control animals. By contrast, aggregation of platelets from Arg animals was reduced by 50%.

This reduction in platelet aggregation was associated with a twofold greater cGMP content in aggregated platelets from arginine-treated animals. The reduction of platelet reactivity could be reversed by administration of N-methylarginine ($10^{-4}$M) in vitro. Therefore, the antiplatelet effect of chronic oral arginine administration can be credited to an increased synthesis of endogenous NO. Furthermore, NO synthesis may be induced in both the platelets and the endothelium.

EXAMPLE 3

Inhibition of monocyte adherence:

A. Functional Binding Assay: To determine if oral arginine supplementation affects monocyte adherence, blood was collected from rabbits fed normal chow (=6) a 1% cholesterol diet (=6), or a 1% cholesterol diet supplemented with L-arginine (=6), as described above. Mononuclear cells were purified from blood by Ficoll-paque density gradient centrifugation. In these preliminary studies, adhesion was examined of blood leukocytes to a transformed endothelial cell line, bEnd3 (mouse brain-derived polyoma middle T antigen transformed endothelial cells were examined). The Bend3 cells display the morphology of endothelial cells, and like human endothelial cells are capable of uptake of acetylated low-density lipoprotein and express adhesion molecules in a cytokine-regulable fashion. Cultured cells were grown to confluence 0.5 cm$^2$ Lab-Tek chamber slides (MilesScientific) and treated with control medium or with LPS (1 mg/ml) or TNF$\alpha$ (25 U/ml) for 18 hours. Cultures were washed with fresh assay buffer, and low, medium, or high concentrations of leukocytes (0.75, 1.5, or $3 \times 10^5$ cells/ml, respectively) were added per well. Following a 30-minute incubation on a rocking platform at room temperature to allow binding, the slides were inverted and immersed in buffer containing 2% (v/v) glutaraldehyde, such that non-adherent cells were lost and adherent cells were fixed to the monolayer. The adherent mononuclear cells were enumerated using video-light microscopy.

Monocytes from hypercholesterolemic animals (Chol) exhibited greater adherence, consistent with observation by others, that monocytes from hypercholesterolemic cats or humans exhibit greater adherence to cultured endothelial cells. (deGruijter, et al. (1991) Metabol. Clin. Exp. 40, 1119–1121; Fan, et al. (1991) Virchows Arch. B Cell Pathol. 61, 19–27).

In comparison to monocytes derived from vehicle-treated hypercholesterolemic animals (Chol), those from arginine-treated hypercholesterolemic animals (Arg) were much more adherent. This data shows that the arginine treatment inhibits adhesion of monocytes to the endothelium, which is the first observable event in atherogenesis.

EXAMPLE 4

Exclusion of the Effect of Enhanced Nitrogen or Caloric Balance as Causing the Observed Results:

To exclude an effect of L-arginine on nitrogen or caloric balance as the cause of these results, six animals received 1% cholesterol diet supplemented by additional methionine to increase the dietary methionine six-fold. At ten weeks animals were sacrificed for studies of platelet and vascular reactivity, and histomorphometry. Endothelium-dependent relaxation, platelet aggregation and intimal thickness were not different than those of animals fed 1% cholesterol diet alone. These results reveal that another amino acid, methionine (which is not a precursor of NO) does not mimic the effect of the amino acid L-arginine. Therefore lit seems likely that the effect of L-arginine is due to its metabolism to nitric oxide, rather than some other effect of amino acid administration (i.e. change in nitrogen or caloric balance).

EXAMPLE 5

Effect of NO synthase expression on proliferation of vascular smooth muscle cells:

Cultured rat aortic vascular smooth muscle cells under confluent quiescent conditions were studied. An efficient viral coat protein-mediated DNA transfer method was employed to transfect the cells with the NO synthase gene driven by the $\beta$-actin promoter and CMV enhancer. This resulted in increased NO synthase activity (as measured by the arginine-to-citrulline conversion assay) in comparison to control vector transfected cells. Transfection of the NO synthase gene completely abolished serum-stimulated DNA synthesis compared to control vector transfection. These results indicated that increased expression of NO synthase (associated with increased production of NO) inhibits excessive proliferation of vascular smooth muscle cells. This inhibition can be correlated with treatment of atherosclerosis and restenosis.

It is evident from the above results, that by enhancing the nitric oxide levels, by means of nitric oxide precursor compounds or other compounds in the nitric oxide pathway, substantial benefits will ensue to patients with vascular degenerative diseases. This treatment will diminish the formation of atherosclerotic plaque and restenosis, by inhibiting adhesion of monocytes and platelets, and by reducing the proliferation of vascular smooth muscle cells.

By virtue of administering to the host, based on a predetermined regimen, or providing in the host a supply of a component in the synthetic pathway for production of nitric oxide, so as to maintain a mildly elevated level of nitric oxide in the host, particularly at the site to be treated, the incidence of plaque formation can be substantially diminished. This can be achieved in a variety of ways: by oral administration in accordance with a predetermined regimen of various compounds associated with nitric oxide formation, e.g. L-arginine; by administration at the site, in a predetermined regimen of compounds which can produce nitric oxide, either directly or as a result of physiologic action of endogenous compounds, e.g. enzymes; by employing combinations of compounds, which by their action result in the production of nitric oxide; or the like. These individual administrations, can be done independently or in conjunction with a regimen of other compounds associated with the production of nitric oxide.

Alternatively, one may use genetic engineering to introduce a gene associated with a component in the synthetic pathway for production of nitric oxide, e.g. nitric oxide synthase, where the enhanced production of such compounds will have the effect of driving the equilibrium to an enhanced production of nitric oxide. Thus, the subject invention provides a plurality of pathways to enhance the synthesis or action of nitric oxide, or reduce the degradation of nitric oxide, thereby increasing the effect of endogenous nitric oxide to prevent the formation of vascular lesions and to inhibit restenosis.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of inhibiting the development of atherosclerosis or restenosis in the vascular system of a human host susceptible to atherosclerosis or restenosis, said method comprising:

administering to said host in accordance with a predetermined regimen a member of the group consisting of L-arginine, its physiologically acceptable salts and biologically equivalent compound thereof for enhancement of NO production by NO synthase in an amount sufficient to enhance the level of endogenous NO in the vascular system.

2. A method according to claim 1, wherein said biologically equivalent compound thereof is a peptide comprising L-arginine.

3. A method according to claim 1, wherein L-arginine is administered.

4. A method according to claim 2, wherein said L-arginine or physiologically acceptable salt is present in a health bar at from about 2-25 g.

5. A method according to claim 1, wherein a physiologically acceptable salt of L-arginine is administered.

* * * * *

UNITED STATES PATENT AND TRADEMARK OFFICE
CERTIFICATE OF CORRECTION

PATENT NO. : 5,428,070
DATED : Jun. 27, 1995
INVENTOR(S) : John P. Cooke, Victor J. Dzau & Gary H. Gibbons It is certified that error appears in the above-identified patent and that said Letters Patent is hereby corrected as shown below:

On title page, item [54] and col. 1, lines 1 – 4, should read as follows:

--[54] TREATMENT OF VASCULAR DEGENERATIVE DISEASES BY MODULATION OF ENDOGENOUS NITRIC OXIDE PRODUCTION OR ACTIVITY--

Signed and Sealed this

Nineteenth Day of September, 1995

Attest:

BRUCE LEHMAN

Attesting Officer    Commissioner of Patents and Trademarks

UNITED STATES PATENT AND TRADEMARK OFFICE
CERTIFICATE OF CORRECTION

PATENT NO. : 5,428,070

DATED : 27 June 1995

INVENTOR(S) : John P. Cooke, Victor J. Dzau & Gary H. Gibbons

It is certified that error appears in the above-indentified patent and that said Letters Patent is hereby corrected as shown below:

In the claims, column 12, lines 22-24, Claim 4 should read as follows:

--A method according to Claim 1, wherein said L-arginine or physiologically acceptable salt thereof is present in a health bar at from about 2-25 g.--

Signed and Sealed this

Fifteenth Day of October, 1996

*Attest:*

BRUCE LEHMAN

*Attesting Officer*   *Commissioner of Patents and Trademarks*

UNITED STATES PATENT AND TRADEMARK OFFICE
CERTIFICATE OF CORRECTION

PATENT NO. : 5,428,070
DATED : June 27, 1995
INVENTOR(S) : J.P. Cooke, V.J. Dzau and G.H. Gibbons It is certified that error appears in the above-identified patent and that said Letters Patent is hereby corrected as shown below:

In column 1, lines 8-9, replace "Grant 1KO7HCO266((NHLBI)" with --Grants 1KO7HCO2660 and HL02668, both awarded by the National Institutes of Health--.

Signed and Sealed this

First Day of August, 2000

Attest:

Q. TODD DICKINSON

*Attesting Officer*    *Director of Patents and Trademarks*